United States Patent
Miller et al.

(10) Patent No.: US 9,744,510 B2
(45) Date of Patent: *Aug. 29, 2017

(54) NITRIC OXIDE GENERATOR AND NON-DELIQUESCENT TABLET FOR USE IN SAME

(71) Applicant: SYK TECHNOLOGIES, LLC, Newport Beach, CA (US)

(72) Inventors: J. W. Randolph Miller, Orem, UT (US); Christie W. Jones, Chula Vista, CA (US)

(73) Assignee: SYK TECHNOLOGIES, LLC, Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/194,861

(22) Filed: Jun. 28, 2016

(65) Prior Publication Data

US 2016/0354745 A1 Dec. 8, 2016

Related U.S. Application Data

(60) Division of application No. 14/803,308, filed on Jul. 20, 2015, which is a division of application No. 14/050,022, filed on Oct. 9, 2013, now Pat. No. 9,107,860, which is a continuation of application No. 13/100,186, filed on May 3, 2011, now Pat. No.

(Continued)

(51) Int. Cl.
| | |
|---|---|
| *B01J 7/00* | (2006.01) |
| *C01B 21/24* | (2006.01) |
| *A61K 33/00* | (2006.01) |
| *A61M 16/12* | (2006.01) |

(52) U.S. Cl.
CPC ............... *B01J 7/00* (2013.01); *A61K 33/00* (2013.01); *A61M 16/12* (2013.01); *C01B 21/24* (2013.01); *B01J 2219/00121* (2013.01); *B01J 2219/00135* (2013.01)

(58) Field of Classification Search
CPC ........................................................ B01J 7/00
See application file for complete search history.

(56) References Cited

U.S. PATENT DOCUMENTS

| | | | |
|---|---|---|---|
| 2,310,907 A | 2/1943 | McMillian | |
| 5,063,050 A * | 11/1991 | Verdon | ................ A61K 8/0216 424/401 |

(Continued)

FOREIGN PATENT DOCUMENTS

JP            61171998 A         8/1986

OTHER PUBLICATIONS

Ray et al, a new method of preparing nitric oxide, 1956, j. am. chem. soc. 78(23) p. 5993.*

(Continued)

*Primary Examiner* — Melvin C Mayes
*Assistant Examiner* — Stefanie Cohen
(74) *Attorney, Agent, or Firm* — Pate Baird, PLLC

(57) ABSTRACT

An apparatus to generate nitric oxide is disclosed in one embodiment in accordance with the invention as including a heat source and a vessel containing the heat source. A tablet may be placed within the vessel such that it is in thermal communication with the heat source to receive heat therefrom. The tablet may contain reactants that are substantially non-deliquescent and form nitric oxide in response to heat from the heat source.

18 Claims, 8 Drawing Sheets

Related U.S. Application Data 8,574,531, which is a continuation of application No. 11/751,523, filed on May 21, 2007, now Pat. No. 7,939,045, which is a continuation-in-part of application No. 10/733,805, filed on Dec. 10, 2003, now Pat. No. 7,220,393.

(56) References Cited

U.S. PATENT DOCUMENTS

| | | | |
|---|---|---|---|
| 5,485,827 | A | 1/1996 | Zapol et al. |
| 5,648,101 | A | 7/1997 | Tawashi |
| 5,839,433 | A | 11/1998 | Higenbottam |
| 5,873,359 | A | 2/1999 | Zapol et al. |
| 5,900,433 | A | 5/1999 | Igo et al. |
| 6,089,229 | A | 7/2000 | Bathe et al. |
| 6,103,275 | A | 8/2000 | Seitz et al. |
| 6,432,077 | B1 | 8/2002 | Stenzler |
| 6,689,810 | B2 | 2/2004 | Martin |
| 6,793,644 | B2 | 9/2004 | Stenzler |
| 7,025,869 | B2 | 4/2006 | Fine et al. |
| 7,040,313 | B2 | 5/2006 | Fine et al. |
| 7,048,951 | B1 | 5/2006 | Seitz et al. |
| 7,939,045 | B2 * | 5/2011 | Miller ............... B01J 7/00 423/405 |
| 8,574,531 | B2 | 11/2013 | Miller et al. |
| 9,107,860 | B2 | 8/2015 | Miller et al. |
| 2001/0037810 | A1 * | 11/2001 | Fine ............... A61K 33/00 128/203.26 |
| 2002/0132730 | A1 * | 9/2002 | Hwang ............ A47L 19/04 502/212 |

OTHER PUBLICATIONS

Ray, James D., Ogg Jr., Richard A. "A new method of Preparing Nitric Oxide" Department of Chemistry, Stanford University, as early as Jul. 25, 1956.

"Guidance for Industry and for FDA Reviews—Guidance Document for Premarket Notification Submissions for Nitric Oxide Delivery Apparatus, Nitric Oxide Analyzer and Nitrogen Dioxide Analyzer," U.S. Food and Drug Administration Center for Devices and Radiological Health, Jan. 24, 2000, Updated Mar. 29, 2007, pp. 1-34, http://www.fda.gov/cdrh/ode/1157.html.

"VIASYS Healthcare Inc. and INO Therapeutics, LLC Reach Settlement" Business Wire, May 14, 2004, pp. 1-2, Conshohocken, PA and Clinton, N. J., http:findarticles.com/p/aricles mi_m0EIN/is_2004_May_14/ai_n6028801.

\* cited by examiner

NITRIC OXIDE GENERATOR AND NON-DELIQUESCENT TABLET FOR USE IN SAME

RELATED APPLICATIONS

This application is a divisional (continuation) of U.S. patent application Ser. No. 14/803,308, filed Jul. 20, 2015, now issued as U.S. Pat. No. 9,486,477; which is a continuation of U.S. patent application Ser. No. 14/050,022, filed Oct. 9, 2013, now issued as U.S. Pat. No. 9,107,860 on Aug. 18, 2015; which is a continuation of U.S. patent application Ser. No. 13/100,186, filed May 3, 2011, now issued as U.S. Pat. No. 8,574,531 on Nov. 5, 2013; which is a continuation of U.S. patent application Ser. No. 11/751,523, filed May 21, 2007, now issued as U.S. Pat. No. 7,939,045 on May 10, 2011; which is a continuation-in-part of U.S. patent application Ser. No. 10/733,805, filed Dec. 10, 2003, now issued as U.S. Pat. No. 7,220,393 on May 22, 2007; all of which are hereby incorporated by reference.

BACKGROUND

1. The Field of the Invention

This invention relates to nitric oxide therapy and more particularly to apparatus and methods for generating and delivering nitric oxide.

2. Background

Although it is one of the simplest biological molecules in nature, nitric oxide plays a significant role in nearly every phase of biology and medicine. From its role as a critical endogenous regulator of blood flow and thrombosis, to a principal neurotransmitter mediating erectile function, to a major pathophysiological mediator of inflammation and host defense, there are few pathological conditions where nitric oxide does not play a significant role. Discoveries relating to nitric oxide have prompted vigorous research in a variety of fields including chemistry, molecular biology, and gene therapy. In just the last two decades, tens of thousands of scientific papers addressing various aspects of this molecule have been published, most of these within the last decade.

One method for delivering nitric oxide to the body is by inhaling therapeutic doses (e.g., 20 to 100 ppm) of nitric oxide gas. This delivery method has been introduced and studied over the last decade to treat conditions such as pulmonary hypertension, hypoxemia, respiratory distress syndrome in newborns, and sickle cell disease. Providing nitric oxide in the respiratory gas dilates pulmonary vessels by relaxing vascular smooth muscle cells. This decreases pulmonary vascular resistance and redistributes pulmonary blood flow to reduce pulmonary arterial pressure and improve arterial oxygenation.

Currently, various methods have been disclosed for generating nitric oxide, including production with polymers or electrochemical production with aqueous solutions of nitric oxide precursors. One method for producing nitric oxide was disclosed in 1956 in a paper titled "A New Method of Preparing Nitric Oxide" authored by James D. Ray and Richard A. Ogg Jr. In that paper, the authors disclosed a method for generating nitric oxide that involves heating a dry powdered mixture of potassium nitrite, potassium nitrate, chromic oxide, and ferric oxide with a yellow flame. The powder was optionally mixed with water to form a stiff paste which could be molded and dried to form cylindrical shapes or pellets. The resulting nitric oxide gas was very pure, in some cases as much as 99.78 percent pure.

Nevertheless, the composition disclosed by Ray and Ogg is not suitable to produce a stable, long-lasting tablet for generating nitric oxide. In particular, the potassium nitrite is deliquescent, tending to absorb excessive amounts of water from the atmosphere causing the material to liquefy. Other ingredients, such as the ferric oxide, are not readily compressed to form a tablet with acceptable friability and hardness.

In view of the foregoing, what is needed is a method and apparatus to produce a stable, long-lasting tablet that will release nitric oxide in suitable quantities, predictably, over a suitable time upon being heated. Further needed is an apparatus for heating and capturing nitric oxide generated by such a tablet. Further needed is an apparatus for diluting the nitric oxide to a therapeutically safe level. Yet further needed is a tablet having acceptable hardness and friability that can be manufactured in large quantities by mass production, distributed, stored, and easily used. Further needed is a tablet that will produce nitric oxide with acceptable efficiency. Yet further needed are methods, materials, and techniques to improve upon the method and composition disclosed by Ray and Ogg.

BRIEF SUMMARY OF THE EMBODIMENTS

Consistent with the foregoing, and in accordance with the invention as embodied and broadly described herein, an apparatus to generate nitric oxide is disclosed in one embodiment in accordance with the invention as including a heat source and a vessel containing the heat source. A tablet may be placed within the vessel such that it is in thermal communication with the heat source to receive heat therefrom. The tablet may contain reactants that are substantially non-deliquescent and form nitric oxide in response to heat from the heat source.

In selected embodiments, the tablet further comprises an inert binder providing a substantially solid path of thermal conduction between granules of reactants. The tablet may be compressed to a hardness providing a thermal conductivity effective to heat the reactants internal thereto substantially exclusively by thermal conduction. In certain embodiments, the hardness of the tablet is selected to be greater than 5 kiloponds. In other embodiments, the hardness of the tablet is selected to be greater than 9 kiloponds. In yet other embodiments, the hardness of the tablet is selected to be from about 10 kiloponds to about 20 kiloponds.

In certain embodiments, the heat source is controlled to melt, yet avoid vaporizing, one or more of the reactants. In other embodiments, the heat source is controlled to melt one or more of the reactants, and to avoid vaporizing any of the reactants.

In certain embodiments, the reactants consist substantially of a non-deliquescent nitrite compound, a nitrate compound, and a single metal oxide. In selected embodiments, the inert binder may include calcium silicate. In other embodiments, the non-deliquescent nitrite compound may include sodium nitrite. Similarly, the nitrate compound may include potassium nitrate and the metal oxide may include chromic oxide.

In a second aspect of the invention, a stable nitric-oxide-producing tablet may include substantially non-deliquescent reactants forming nitric oxide in response to heat applied thereto. These reactants may include a non-deliquescent nitrite compound, a nitrate compound, and a metal oxide. The tablet may also include an inert binder providing a substantially solid path of thermal conduction between the reactants.

In selected embodiments, the inert binder may include calcium silicate. In other embodiments, the non-deliquescent nitrite compound may include sodium nitrite. Similarly, the nitrate compound may include potassium nitrate and the metal oxide may include chromic oxide.

In a third aspect of the invention, a method of generating nitric oxide may include providing a solid tablet comprising non-deliquescent reactants. This tablet may then be heated to melt at least one of the reactants to promote reaction thereof, thereby generating nitric oxide. The nitric oxide may then be mixed with a diluent gas to provide a therapeutically safe and effective concentration of nitric oxide.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments in accordance with the invention and are, therefore, not to be considered limiting of its scope, the invention will be described with additional specificity and detail through use of the accompanying drawings in which:

DETAILED DESCRIPTION OF THE EMBODIMENTS

It will be readily understood that the components of the present invention, as generally described and illustrated in the Figures herein, could be arranged and designed in a wide variety of different configurations. Thus, the following more detailed description of the embodiments of apparatus and methods in accordance with the present invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Figure 1:
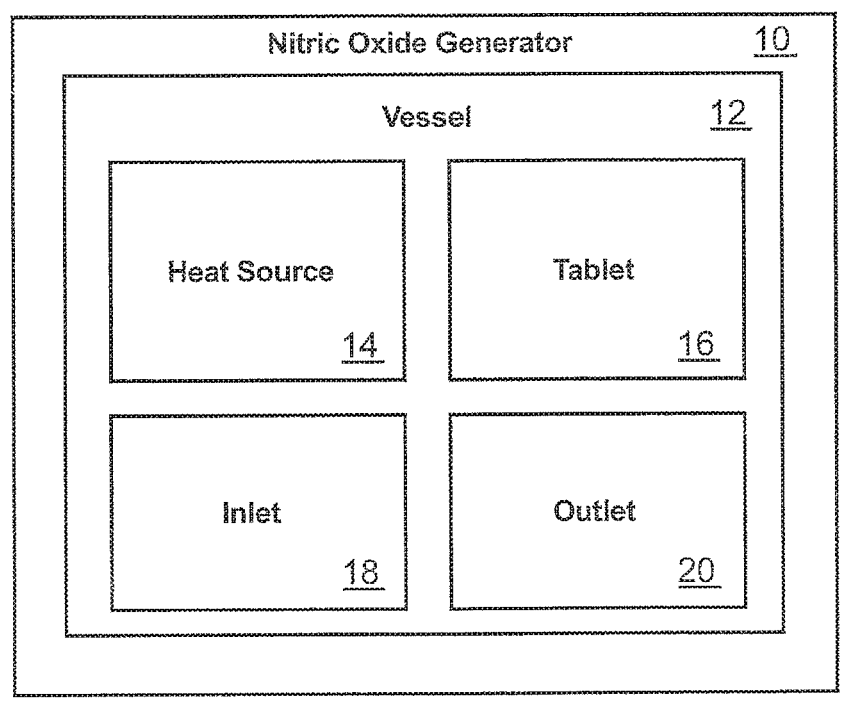
FIG. 1 is a high-level block diagram of one embodiment of a nitric oxide generator in accordance with the invention.

Referring to FIG. 1, in general, a nitric oxide generator 10 in accordance with the invention may include a vessel 12 and a heat source 14 within the vessel 12. The heat source 14 may be in thermal communication with a tablet 16. The tablet 16 may contain reactants that generate nitric oxide gas when heated. The reactants in the tablet 16 may be depleted after heating the tablet 16 for a given time and temperature, after which the tablet 16 may be replaced. In selected embodiments, the tablet 16 may retain its shape and structure after the reactants have been substantially depleted.

The heat source 14 may be in direct contact with the tablet 16 to conduct heat directly to the tablet 16. Alternatively, the heat source 14 may radiate heat, which may then be absorbed by the tablet 16 without physical contact. In either case, the heat source 14 may be placed inside the vessel 12 in order to efficiently transfer heat to the tablet 16. This may also provide a degree of safety when handling or coming into contact with the generator 10. In selected embodiments, the nitric oxide generator 10 may also include an inlet 18 to allow diluent gases to enter the vessel 12 and thereby mix with and dilute the nitric oxide gas. The resulting diluted nitric oxide gas may then exit the vessel 12 through an outlet 20 where it may be stored or conveyed to a person or animal to provide therapy.

Figure 2A:
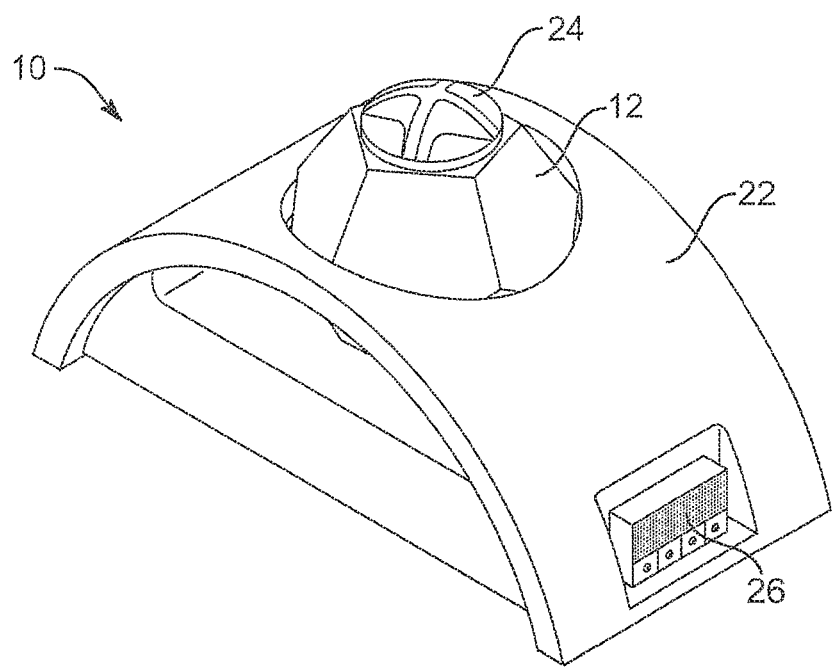
FIG. 2A is a front perspective view of one embodiment of an implementation of a nitric oxide generator in accordance with the invention.
Figure 2B:
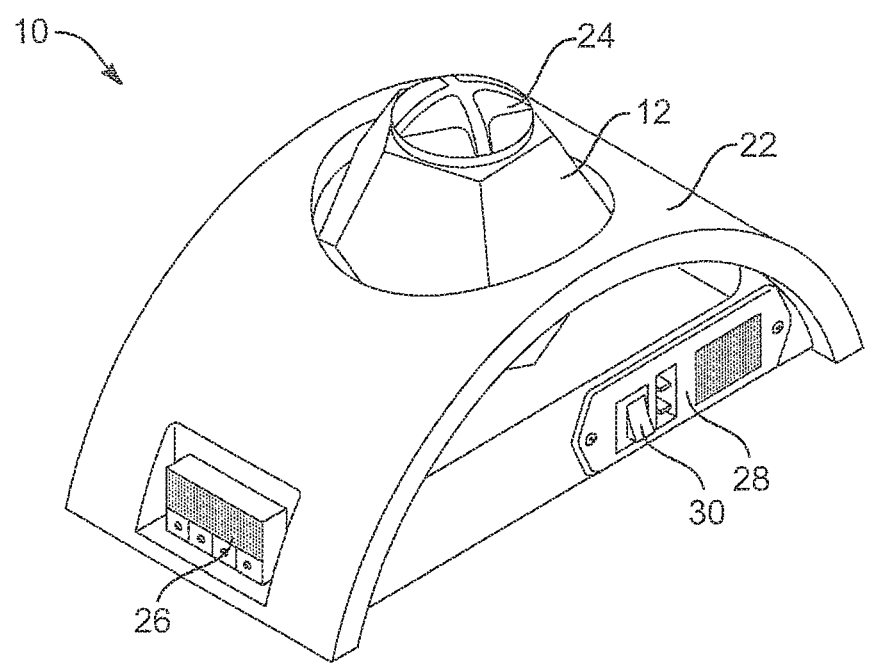
FIG. 2B is a rear perspective view of the nitric oxide generator illustrated in FIG. 2A.

Referring to FIGS. 2A and 2B, one specific and non-limiting implementation of a nitric oxide generator 10 in accordance with the invention is illustrated. As shown, in one embodiment a nitric oxide generator 10 may include a body portion 22 which may support a vessel 12. In this embodiment, the vessel 12 is provided in the form of a clam shell which may include separable upper and lower portions. These portions may be separated to provide access to the heat source 14 and allow tablets 16 to be inserted or replaced. In selected embodiments, a thumbscrew 24 or clamp 24 may be used to keep the upper and lower portions of the clam shell together to seal the vessel 12 and prevent injury. As will be shown in FIG. 3, the clam shell may also include one or more inlets 18 and outlets 20 to allow diluent gases to enter the vessel 12, mix with nitric oxide gas, and exit the vessel 12. These inlets 18 and outlets 20 may, in certain embodiments, be fitted with a latch, coupling, fitting, or other connector to connect to a hose or other device.

In selected embodiments, a generator 10 may also include a control panel 26 to adjust various operational parameters of the nitric oxide generator 10. For example, the control panel 26 may be used to adjust the temperature, current, or heat output of the heat source 14 which may in turn adjust the amount of nitric oxide produced. This may be used to adjust the concentration of nitric oxide in gases exiting the vessel 12. In other embodiments, the control panel 26 may be used to regulate the flow of diluent gases through the vessel 12 with a valve or other control device. This may also adjust the concentration of nitric oxide in gases exiting the vessel 12. In other embodiments, the control panel 26 may be used to turn the generator 10 on or off, set a timer to turn the generator 10 on or off, set a temperature, current, or heat profile for the heat source 14 that changes (e.g. monotonically or programmatically) over time 14, or the like. Similarly, the control panel 26 may be configured to trigger one or more alarms when the nitric oxide concentration rises above or falls below a selected threshold. These examples represent just a few possible functions for a control panel 26.

The generator 10 may also include a power supply panel 28 connecting to a power cord or other source of electricity. A switch 30 may be provided to selectively connect or interrupt the supply of power to the generator 10.

Figure 3:
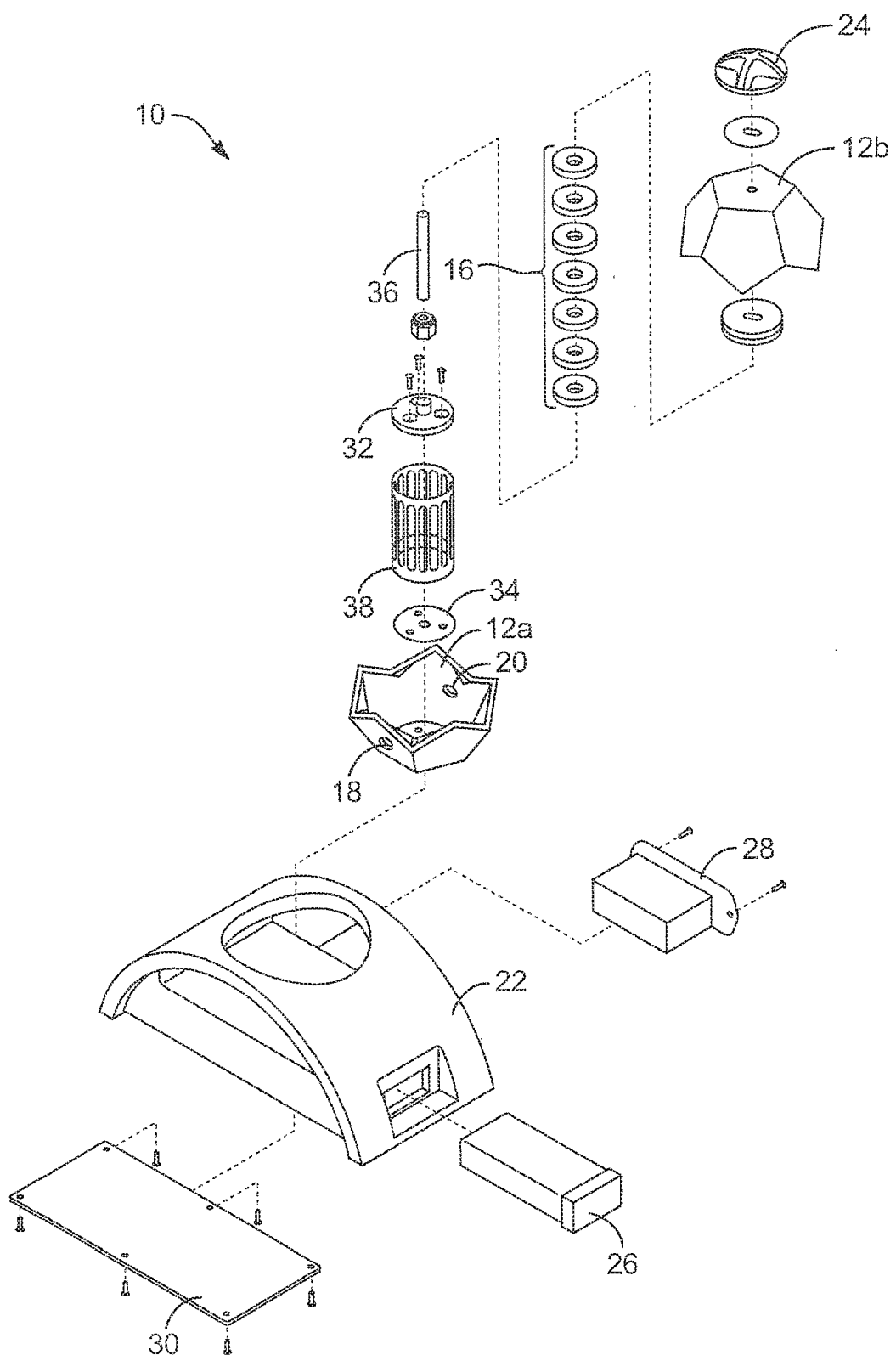
FIG. 3 is an exploded perspective view of the nitric oxide generator illustrated in FIGS. 2A and 2B.

Referring to FIG. 3, an exploded view of the generator 10 of FIGS. 2A and 2B is illustrated. As shown, the generator 10 may include a body portion 22, a control panel 26, and power supply panel 28, which may be inserted into the body portion 22. A cover plate 30 may be used to provide access to the control panel 26, power supply 28, and possibly a heating element 36 from below the generator 10. A vessel 12, in this example a selectively opened and closed clam shell 12a, 12b, may be inserted into or mounted to the body portion 22. A lower portion 12a of the vessel 12 may be attached to the body portion 22 using a mounting plate 32, washer 34, and one or more fasteners, such as screws, rivets, welds, or the like. The lower portion 12a may include one or several ports, such as an inlet 18 and outlet 20, to allow diluent gases to pass through the vessel 12.

In selected embodiments, a heating element 36, such as a calrod 36 or cartridge heater 36, may be inserted through the mounting plate 32 and washer 34 where it may be connected to a power source outside the vessel 12a, 12b. One or more tablets 16, having apertures therein, may be placed over the heating element 36. The tablets 16 may be stacked directly on top of one another or may be separated by a washer or other spacer. The tablets 16 may be heated through direct contact with the heating element 36 or may, alternatively, absorb heat radiated from the heating element 36. The temperature of the heating element 36 may be controlled to provide a regulated amount of heat (e.g., between 200° C. and 700° C.) to the tablets 16. This enables nitric oxide to be generated over a period of time and in a controlled manner.

In selected embodiments, the tablets 16 may be surrounded by a perforated baffle 38. The baffle 38 may regulate heat dissipation from the tablets 16, provide more uniform heating of the tablets 16, regulate the flow of diluent gases over the tablets 16, or the like. The baffle 38, by contrast, may allow nitric oxide gas to pass through slots or apertures in the baffle 38 to mix with diluent gases passing through the vessel 12.

An upper portion 12b of the vessel may be used to cover the heating element 36 and tablets 16, seal the vessel 12, prevent the escape of nitric oxide, and retain heat within the vessel 12. The upper portion 12b may be retained over the lower portion 12a by, for example, a thumbscrew 24, clamp 24, or other suitable retention mechanism.

Figure 4:
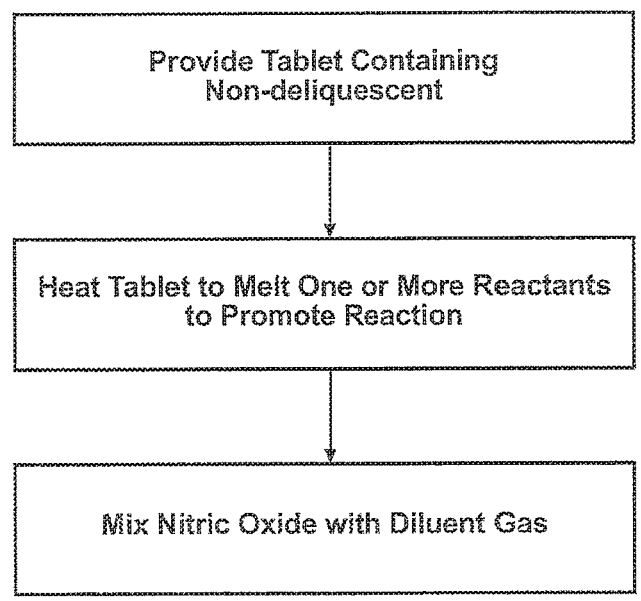
FIG. 4 is a flow chart of one embodiment of a method for generating nitric oxide.

Referring to FIG. 4, in selected embodiments, a method 50 for generating nitric oxide may include providing 52 one or more tablets 16 containing non-deliquescent reactants for producing nitric oxide. Use of non-deliquescent reactants enables manufacture of an environmentally stable tablet 16 that will retain its ability to produce nitric oxide over time. As will be explained in more detail hereafter, the stability of the reactants enable production of a tablet 16 that is both harder and less friable than may be possible with deliquescent reactants. Additional hardness, which may be a function of the amount of compressive force applied to the tablet 16, may increase the nitric oxide production of the tablet 16 by improving the solidity and thus thermal conductivity of the tablet 16. As will be explained in more detail hereafter, this provides a tablet 16 having improved stability and an improved ability to produce nitric oxide, and to do so more predictably, compared to a tablet 16 containing one or more deliquescent reactants, such as potassium nitrite.

Once a tablet 16 is provided 52, the method may include heating 54 the tablet 16 to melt one or more reactants. This may cause the melted reactants to come into intimate molecular contact, and even to migrate through the tablet until they come into contact with other reactants, thereby initiating the nitric-oxide producing reaction. This also enables certain ones of the reactants to be reacted as liquids (or vapors, or both) with heat of a fairly modest temperature (e.g., 300-500° C.). In certain embodiments, reactants may be vaporized to react in a vapor phase. In selected embodiments, the substantially non-deliquescent reactants may include sodium nitrite, potassium nitrate, and chromium oxide. These reactants may produce nitric oxide in accordance with the following stoichiometric equation:

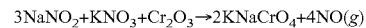

$$3NaNO_2 + KNO_3 + Cr_2O_3 \rightarrow 2KNaCrO_4 + 4NO(g)$$

Of the above reactants, sodium nitrite ($NaNO_2$) has the lowest melting temperature (270° C.). Thus, upon heating the reactants to 270° C., the sodium nitrite may begin to melt and intermingle with molecules of other reactants. It may even flow through the tablet 16 to make intimate contact with other reactants, thereby initiating the nitric-oxide-producing reaction. In selected embodiments, the temperature may be controlled to avoid vaporizing any of the reactants. Thus, the reaction may occur mostly in the solid and liquid phases of reactants.

For example, sodium nitrite has the lowest boiling point (320° C.) of the reactants. Thus, in certain embodiments the temperature of the heating element 36 may be maintained between about 270° C. and 320° C. to melt the sodium nitrite while avoiding vaporizing it. Thus, a liquid reactant can move to contact solid reactants. By controlling the temperature, the reaction may be controlled to allow the nitric oxide to be released over a desired period of time, such as, for example, about 30 minutes. Nevertheless, in other embodiments, the reactants may be heated to greater temperatures, such as between about 300° C. and 700° C. Thus, although the generator 10 may generate nitric oxide at lower temperatures, its use is not limited to the lower temperatures.

Once the reaction is generating nitric oxide, the resulting nitric oxide gas may be mixed 56 with a diluent gas, such as nitrogen, air, or the like, to dilute the nitric oxide to a therapeutically safe level, such as between about 20 and about 500 ppm. A range of about 250 to about 400 ppm is particularly useful, with a target of just over 300 ppm. In selected embodiments, the diluent gas may be pumped into the vessel 12 at a desired rate (e.g., 0.5 L/min) where it may mix with the nitric oxide and exit through an outlet 20. In other embodiments, the nitric oxide may be drawn into a stream of diluent gas using a principle such as the venturi effect.

Figure 5A:
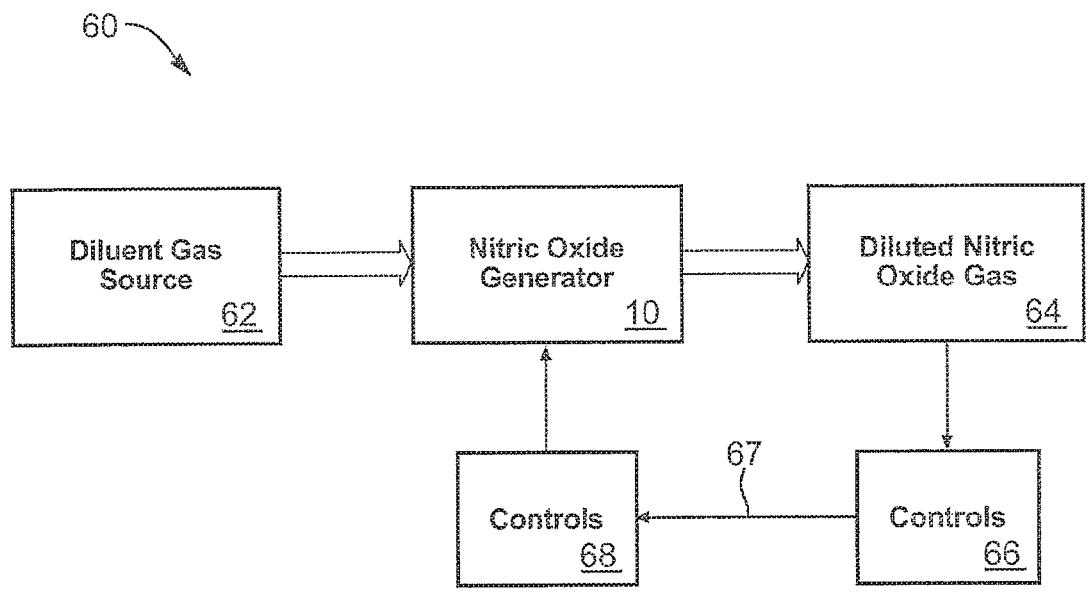
FIG. 5A is a high-level block diagram of one embodiment of a feedback system for use with a nitric oxide generator in accordance with the invention.

Referring to FIG. 5A, in selected embodiments, a nitric oxide generation system 60 may include a diluent gas source 62, a nitric oxide generator 10, and a destination for diluted nitric oxide gas 64. In certain embodiments, the system 60 may utilize a feedback loop to control the concentration of nitric oxide gas in the diluted nitric oxide gas 64. For example, one or more sensors 66 may be used to sense the concentration of nitric oxide in the diluted nitric oxide gas 64. These sensors may provide a feedback signal 67 to various controls 68. These controls 68 may be used to adjust the temperature of a heating element 36 of the nitric oxide generator 10. By adjusting the temperature, heat, current, or other energy control point, the speed of the reaction and thus the nitric oxide release rate may be adjusted to achieve a desired concentration of nitric oxide in the diluted gas 64.

Figure 5B:
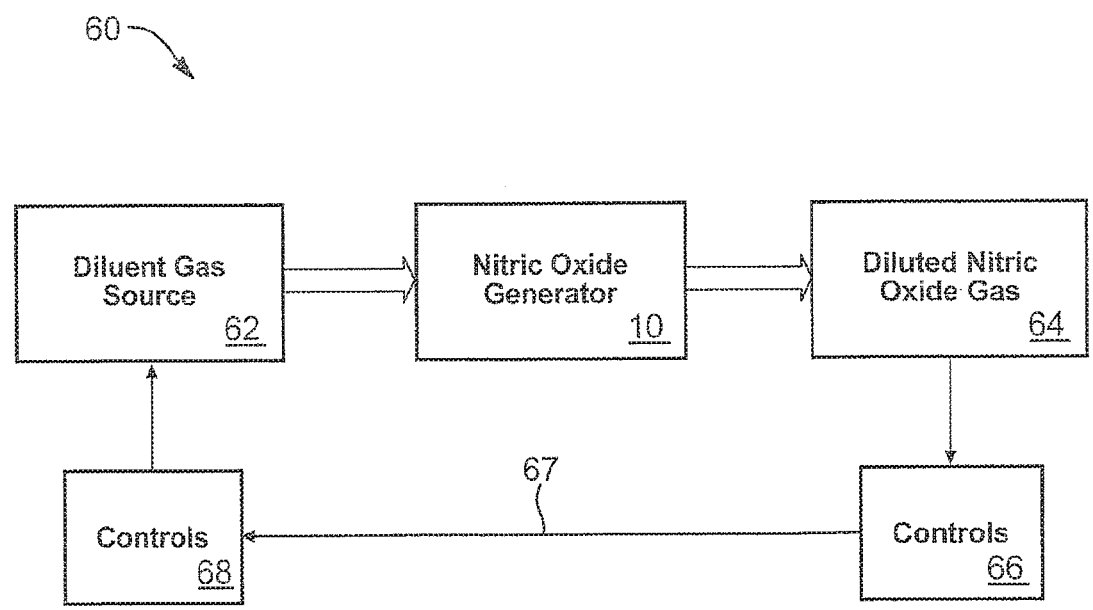
FIG. 5B is a high-level block diagram of another embodiment of a feedback system for use with a nitric oxide generator in accordance with the invention.

Referring to FIG. 5B, in an alternative embodiment, a feedback signal 67 may be used to control the flow rate of a diluent gas through the nitric oxide generator 10. This may also adjust the concentration of nitric oxide in the diluted gas 64. This may be accomplished, for example, by adjusting the speed of a pump moving the diluent gas. Alternatively, the feedback signal may be used to control a valve to regulate the flow rate of diluent gases through the nitric oxide generator 10. In selected embodiments, a system 60 may utilize both types of feedback illustrated in FIGS. 5A and 5B to control the concentration of nitric oxide in the stream or supply of diluted gas 64.

Figure 6:
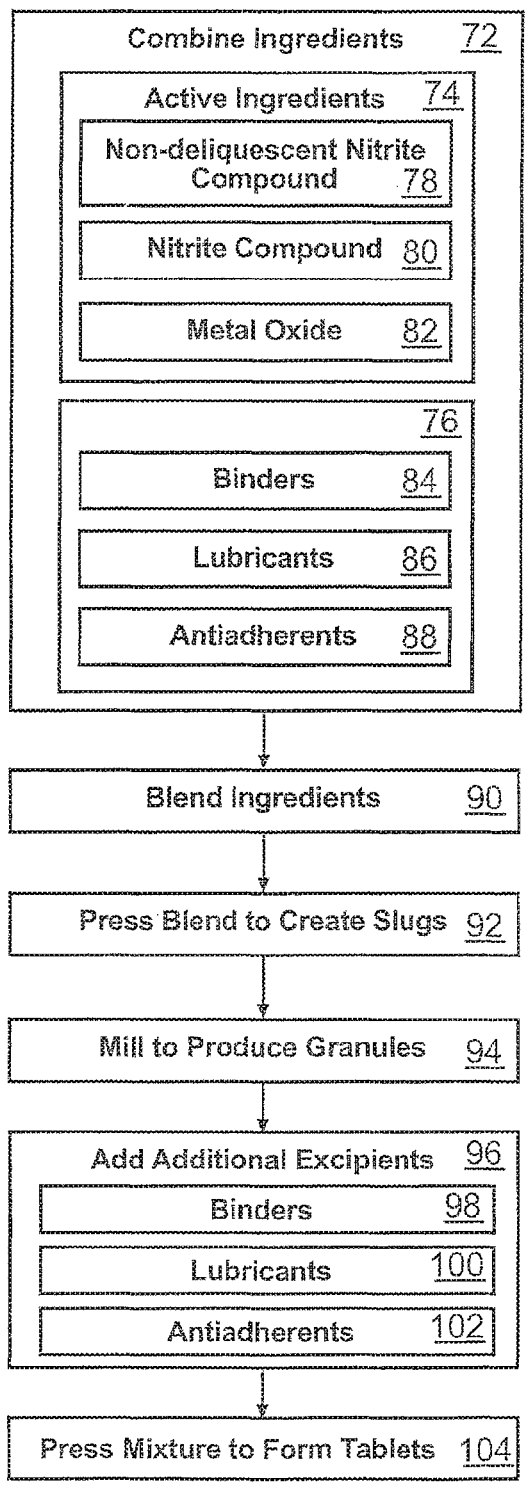
FIG. 6 is a flow chart of one embodiment of a method for creating a non-deliquescent nitric-oxide-producing tablet in accordance with the invention.

Referring to FIG. 6, one embodiment of a method 70 for making a nitric-oxide-producing tablet 16 using a dry granulation process is illustrated. In certain embodiments, such a method 70 may include initially combining 72 various ingredients, such as active ingredients 74 and excipients 76, to produce a tablet 16. In selected embodiments, active ingredients may include a non-deliquescent nitrite compound 78, a nitrate compound 80, and a metal oxide 82. In one embodiment, the active ingredients may include about 33 percent by weight of sodium nitrite, about 17 percent by weight of potassium nitrate, and about 50 percent by weight of chromic oxide. A stoichiometric mixture may be used or an excess of all ingredients except for a rate controlling reactant.

The tablet 16 may also include one or more excipients 76 that may improve the manufacturability of the tablet 16 as well as increase the thermal conductivity, heat transfer capacity, or temperature uniformity, and thus nitric oxide production, of the tablet 16. For example, the tablet 16 may include one or more binders 84, lubricants 86, and antiadherents 88. In one embodiment, a suitable binder 84 may include calcium silicate ($Ca_2SiO_4$), a suitable lubricant 86 may include zinc stearate, and a suitable antiadherent 88 may include talc to prevent punch sticking. The calcium silicate acts a compression aid to produce a tablet 16 with acceptable hardness and friability. The calcium silicate does not replace the ferric oxide disclosed by Ray and Ogg. It serves a different function without harming nitric oxide production. In fact, ferric oxide was found to be detrimental to tablet 16 physical properties, producing tablets 16 with unacceptable brittleness and friability.

In selected embodiments, combining 72 the ingredients may include initially combining all the active ingredients 74 with about half of the excipients 76. These ingredients may then be blended 90 with a device such as a V-blender. This mixture may then be pressed 92 using a tablet or other suitable press to create slugs containing the above-mentioned ingredients. In selected embodiments, the slugs may be pressed to a hardness above about 5 kiloponds. In other embodiments, the slugs may be pressed to a hardness of between about 10 and 20 kiloponds. In other embodiments, the slugs may be pressed to a hardness of about 14 kiloponds.

The compressive force applied to the tablets 16 may be important and may affect the nitric oxide production of the tablets 16. In general, a higher compressive force will improve the nitric oxide production of a tablet 16. Higher compressive forces reduce air volume and improve chemical intimacy between the reactants, as well as increasing the thermal conductivity of the tablet 16 by both conforming particles to one another and removing pores or other voids in the tablet 16. The improved thermal conductivity provides better heat transfer to the reactants, and better molecular contact, thereby providing more uniform heating and better nitric oxide production.

Once created, the slugs may be milled 94, such as with a Fitzmill Model DASO 6, to produce granules. These granules may be filtered through, for example, about a number 20 mesh screen to remove larger particles. The granules, as well as the remaining binder 98, lubricant 100, and antiadherents 102 may then be combined 96 and returned to the blender for mixing. This mixture may then be returned to the tablet press to create 104 the tablets 16. In selected embodiments, a different tool or die may be used to produce tablets 16 with an aperture in the middle, as illustrated in FIG. 3. In certain embodiments, the tablets 16 may be pressed to a final hardness above about 5 kiloponds. In other embodiments, the tablets 16 may be pressed to a hardness of between about 10 and 20 kiloponds. In other embodiments, the tablets 16 may be pressed to a hardness of about 17 kiloponds.

Tablets 16 made in accordance with a method 70 have been found to have greatly improved physical properties. They also exhibit significantly improved nitric oxide production in the generator 10 disclosed by Applicants. That is, the tablets 16 greatly outperform the powders, "pellets," or molded "cylindrical pieces" disclosed by Ray and Ogg when heated in the nitric oxide generator 10. Because of the improved performance, significantly less amounts of active ingredients are required to produce a tablet 16 having acceptable nitric oxide production.

For example, a 5 gram tablet made in accordance with Ray and Ogg's method and containing approximately 85 percent by weight of active ingredients produced only 2.4 mL of nitric oxide gas when heated in the generator 10. By contrast, a five gram tablet 10 made in accordance with a method 70 and containing only 10 percent by weight of active ingredients produced about 11.5 mL of nitric oxide in the generator 10. This constitutes a more than 3000 percent increase in efficiency.

In selected embodiments, a tablet 16 made in accordance with the method 70 and exhibiting vastly improved efficiency may include about 3.3 percent by weight of sodium nitrite, about 1.7 percent by weight of potassium nitrate, about 5 percent by weight of chromic oxide, about 87 percent by weight of calcium silicate, about 2 percent by weight of zinc stearate, and about 1 percent by weight of talc. When compressed to a hardness of about 12.9 kiloponds, a 5 gram tablet 16 having the above composition produced approximately 11.5 mL of nitric oxide and had acceptable friability to create a satisfactory manufactured product.

Figure 7:
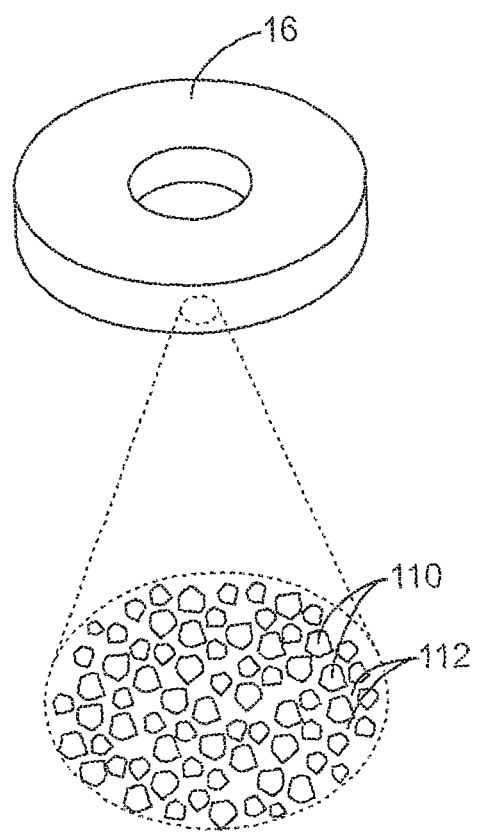
FIG. 7 is an enlarged perspective view of one embodiment of a tablet in accordance with the invention, showing the tablet's granular structure.

Referring to FIG. 7, as mentioned, a tablet 16 in accordance with the invention may be provided as a granulated structure that may actually increase nitric oxide production. For example, as illustrated, reactants within the tablet 16 may be agglomerated into granulated subdomains 110 within the tablet 16. The binder 112 (e.g., calcium silicate) may be present within and between the granules 110. Each of the subdomains 110 may be compressed to a hardness of greater than 5 kiloponds and more ideally between about 10 and 20 kiloponds to create chemical intimacy between the reactants of each granule. As was described in association with FIG. 6, this may be accomplished by creating slugs from a mixture containing the reactants and then milling the slugs to create granules 110 of a desired size. These granules 110 may also improve the flowability of the mixture to prevent the mixture from sticking together, thereby enabling production of a tablet 16 with improved physical characteristics.

As mentioned, the calcium silicate binder is a material that acts as a compression aid when forming the tablet 16. An unexpected benefit provided by the calcium silicate after compression is that it provides an effective path of thermal conduction to the reactants. This path of thermal conduction is provided both intergranularly, by the binder included within each granule 110, as well as extra-granularly, by the binder 112 provided between each granule 110. These paths of thermal conduction provide an effective mechanism to transfer heat to each granule 110 and to the reactants within each granule 110. This enables heat to be more efficiently transported to the reactants, significantly improving nitric oxide production by getting more of the reactants to react with one another. It follows that greater compressive forces applied to the tablet 16 may actually increase the chemical intimacy between the reactants and the binder and thus improve nitric oxide production.

Figure 8:
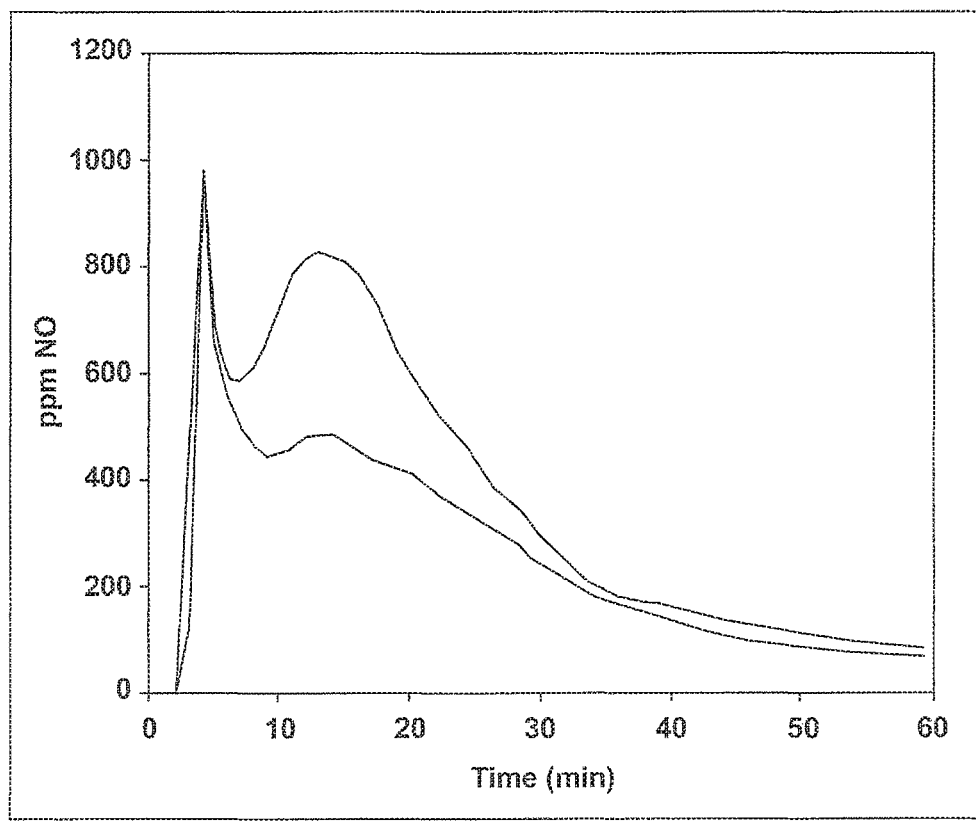
FIG. 8 is a graph showing nitric oxide production of a tablet as a function of time and compression force.

FIG. 8 is a graph showing the effect of compressive force on nitric oxide production. Each of the curves 120a, 120b represents the nitric oxide production of one 5-gram tablet 16 containing 10 percent by weight active ingredients and made in accordance with the method 70 illustrated in FIG. 6. The tablets 16 were heated to about 500° C. in the nitric oxide generator 10 illustrated in FIGS. 2A and 2B with nitrogen gas passing through the unit at a flow rate of about 0.5 L/min. The nitric oxide concentration was measured (in ppm) in the outgoing gas stream, as shown on the vertical axis of the graph.

Both tablets 16 represented by the curves 120a, 120b contain about 3.3 percent by weight of sodium nitrite, about 1.7 percent by weight of potassium nitrate, about 5 percent by weight of chromic oxide, about 89 percent by weight of calcium silicate, and about 1 percent by weight of zinc stearate. The only significant difference between the tablets 16 is that the tablet 16 represented by the curve 120a was compressed to a hardness of about 16.0 kiloponds, whereas the tablet 16 represented by the curve 120b was compressed to a hardness of about 10.0 kiloponds.

As can be seen for both tablets 16, nitric oxide production is greatest at the beginning of production. This production diminishes over the typical (e.g. about 30 to 90 minutes) 60 minute interval during which the reactants are consumed. As can also be observed, the tablet 16 represented by the curve 120a, which was compressed to a hardness of about 16.0 kiloponds, generated significantly more nitric oxide than the tablet 16 represented by the curve 120b and compressed to a hardness of about 10.0 kiloponds. These results bolster the conclusion that greater compressive forces applied to the tablet 16 increase the thermal conductivity, chemical intimacy, or both of the tablets 16 and thus improve nitric oxide production. That is, greater compressive forces achieve nitric oxide yields, in a stream of a breathing gas (e.g. air, nitrogen) having a volume of about half a liter per minute, closer to the theoretical yield. These results also achieve a target yield of at least 300 ppm of nitric oxide for at least 30 minutes.

The present invention may be embodied in other specific forms without departing from its basic features or essential characteristics. The described embodiments are to be considered in all respects only as illustrative, and not restrictive. The scope of the invention is, therefore, indicated by the appended claims, rather than by the foregoing description. All changes within the meaning and range of equivalency of the claims are to be embraced within their scope.

What is claimed is:

1. An apparatus generating nitric oxide, the apparatus comprising:
   a heat source;
   a vessel containing the heat source;
   a tablet, positioned within the vessel and in thermal communication with the heat source to receive heat therefrom; and
   the tablet, comprising at least two reactants capable of forming nitric oxide when heated, wherein at least one reactant is non-deliquescent, and agglomerating the reactants into granulated sub-domains within the tablet.

2. The apparatus of claim 1, wherein the tablet further comprises an inert binder providing a substantially solid path of thermal conduction between granules of reactants.

3. The apparatus of claim 1, wherein the tablet is compressed to a hardness providing a thermal conductivity effective to heat the reactants substantially exclusively by thermal conduction.

4. The apparatus of claim 1, further comprising controlling the heat source to melt, yet avoid vaporizing, at least one of the reactants.

5. The apparatus of claim 3, wherein the hardness of the tablet is selected to be greater than 5 kiloponds.

6. The apparatus of claim 4, wherein the heat source is controlled so as to met, yet avoid vaporizing, any of the reactants.

7. The apparatus of claim 1, wherein the reactants consist essentially of:
   a non-deliquescent nitrite compound;
   a nitrate compound; and
   a single metal oxide.

8. The apparatus of claim 1, wherein the reactants comprise:
   a non-deliquescent nitrite compound;
   a nitrate compound; and
   a metal oxide.

9. The apparatus of claim 2, wherein the inert binder comprises calcium silicate.

10. The apparatus of claim 8, wherein the non-deliquescent nitrite compound comprises sodium nitrite.

11. The apparatus of claim 8, wherein the nitrate compound comprises potassium nitrate and the metal oxide comprises chromic oxide.

12. The apparatus of claim 8, wherein the tablet further comprises a lubricant and an antiadherent.

13. An apparatus generating nitric oxide, the apparatus comprising:
   a heat source;
   a vessel containing the heat source;
   a tablet, positioned within the vessel and in thermal communication with the heat source to receive heat therefrom;
   the tablet, comprising at least three reactants capable of forming nitric oxide when heated, wherein at least one reactant is a non-deliquescent nitrite compound and another reactant is a nitrate compound and another reactant is a metal oxide; and
   the tablet further comprising an inert binder providing a substantially solid path of thermal conduction between granules of reactants.

14. The apparatus of claim 13, further comprising agglomerating the reactants into granulated sub-domains within the tablet.

15. An apparatus for generating nitric oxide, the apparatus comprising:
   a heat source;
   a vessel containing the heat source and a perforated baffle;
   a tablet, positioned within the vessel and surrounded by at least a portion of the perforated baffle and in thermal communication with the heat source to receive heat therefrom; and
   the tablet, comprising at least two reactants capable of forming nitric oxide when heated, wherein at least one reactant is non-deliquescent.

16. The apparatus of claim 15, wherein the reactants comprise:
   a non-deliquescent nitrite compound;
   a nitrate compound; and
   a metal oxide.

17. The apparatus of claim 16, wherein the tablet further comprises an inert binder providing a substantially solid path of thermal conduction between granules of reactants.

18. The apparatus of claim 17, further comprising agglomerating the reactants into granulated sub-domains within the tablet.

\* \* \* \* \*